United States Patent [19]

Chang

[11] Patent Number: 4,994,104
[45] Date of Patent: Feb. 19, 1991

[54] TETRAHYDROPHTHALIMIDE CARBAMATE HERBICIDAL COMPOSITIONS

[75] Inventor: Jun H. Chang, Princeton Junction, N.J.

[73] Assignee: FMC Corporation, Philadelphia, Pa.

[21] Appl. No.: 286,434

[22] Filed: Dec. 19, 1988

[51] Int. Cl.$^5$ .................................... A01N 43/40
[52] U.S. Cl. ........................ 71/94; 71/188; 71/90; 71/92; 71/95; 544/58.4; 544/137; 544/141
[58] Field of Search .............. 544/105, 137, 141, 58.4; 71/90, 94, 95, 88

[56] References Cited

U.S. PATENT DOCUMENTS

| | | | |
|---|---|---|---|
| 4,431,822 | 2/1984 | Nagano et al. | 71/96 |
| 4,521,242 | 6/1985 | Takematsu et al. | 71/94 |
| 4,521,242 | 6/1985 | Takematsu et al. | 71/94 |
| 4,619,687 | 10/1986 | Haga et al. | 71/92 |
| 4,640,707 | 2/1987 | Nagano et al. | 71/96 |
| 4,734,124 | 4/1988 | Chang et al. | 71/92 |
| 4,755,217 | 7/1988 | Chang et al. | 71/93 |
| 4,761,174 | 8/1988 | Chang et al. | 71/92 |
| 4,778,792 | 10/1988 | Lesieur et al. | 544/105 |
| 4,830,659 | 5/1989 | Chang | 71/90 |

FOREIGN PATENT DOCUMENTS 0170191 2/1986 European Pat. Off. .

*Primary Examiner*—Nicholas S. Rizzo
*Assistant Examiner*—Deborah D. Carr

*Attorney, Agent, or Firm*—Robert M. Kennedy; H. Robinson Ertelt; Abner Sheffer

[57] ABSTRACT

Disposed are herbicidal compounds of the formula

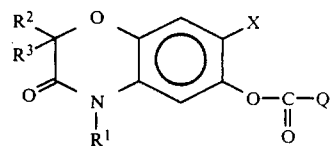

wherein Q is a heterocyclic ring having 5 to 7 ring atoms and having the formula

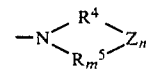

wherein Z is an oxygen or sulfur atom or a vinylene group, $R^4$ and $R^5$ are independently alkylene groups having 1 to 4 carbon atoms, and m and n are each independently an integer of 0 or 1; and in which $R^1$ is H, alkyl, alkenyl, alkynyl, haloalkyl, haloalkenyl, haloalkynyl, alkoxyalkyl, alkoxyalkoxyalkyl, cycloalkyl, aralkyl, alkylthioalkyl, hydroxy, alkoxy, cyanoalkyl or alkylcarbonylalkyl; $R^2$ and $R^3$ are independently H or alkyl; and X is H, Cl or F. Also disclosed are herbicidal compositions and an herbicidal method of use for the herbicidal compounds.

6 Claims, No Drawings

TETRAHYDROPHTHALIMIDE CARBAMATE HERBICIDAL COMPOSITIONS

This invention relates to compounds of the following formula I and their use as herbicides:

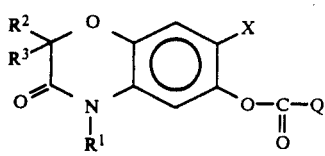

Formula I wherein Q is a heterocyclic ring having 5 to 7 ring atoms and having the formula

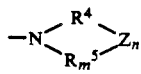

wherein Z is an oxygen or sulfur atom or a vinylene group, $R^4$ and $R^5$ are independently alkylene groups having 1 to 4 carbon atoms, and m and n are each independently an integer of 0 or 1; and in which $R^1$ is:
H;
alkyl e.g. methyl, ethyl or propyl;
alkenyl, e.g. allyl or methylallyl;
alkynyl, e.g. propynyl or methylpropynyl;
haloalkyl, e.g. 3-chloropropyl;
haloalkenyl, e.g. 2-chloropropenyl;
haloalkynyl, e.g. 3-bromopropynyl;
alkoxyalkyl, e.g. methoxymethyl or ethoxymethyl;
alkoxyalkoxyalkyl, e.g. ethoxymethoxymethyl;
cycloalkyl, e.g. cyclopropylmethyl or cyclopropyl;
aralkyl, e.g. benzyl;
alkylthioalkyl, e.g. methylthiomethyl;
hydroxy;
alkoxy, e.g. methoxy or ethoxy;
cyanoalkyl, e.g. cyanomethyl;
alkylcarbonylalkyl, methylcarbonylmethyl;
$R^2$ and $R^3$ are, independently, H or alkyl, e.g. methyl, preferably H; and
X is H, Cl or F, preferably F.
Examples of Q groups which may be employed are

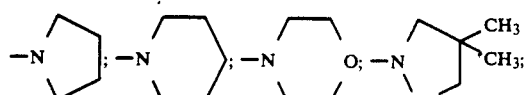

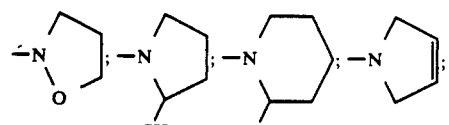

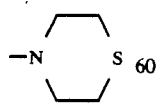

i.e., pyrrolidin-1-yl, piperidin-1-yl, morpholin-1-yl, 4,4-dimethylisoxazolidin-2-yl, isoxazolidin-2-yl, 2-methylpyrrolidin-1-yl, 2-methylpiperidin-1-yl, 3-pyrrolin-1-yl, and thiomorpholin-1-yl.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 carbon atoms, and that any cycloalkyl moiety have 3 to 7 ring carbon atoms.

The compounds of this invention may be prepared by the use of steps generally described in the literature or in the following Example or by methods analogous or similar thereto and within the skill of the art.

In the Example below (Step A), there is formed a compound of the formula

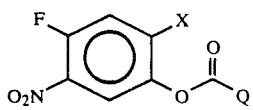

(Formula II)

which (in Step B) is treated to introduce an alkoxycarbonylmethoxy or similar group at the 4-position of the benzene ring (by displacement of F) to form a compound of the formula

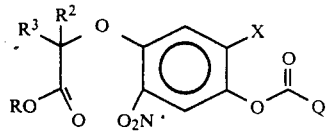

(Formula III)

where OR is alkoxy or a similar group which can be displaced in a subsequent ring-closure reaction. Then (in Step C) reduction of the nitro group to an amino group, followed by ring closure, forms a compound of the formula

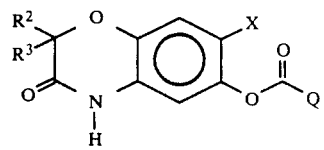

(Formula IV)

The compound of Formula IV is then treated (Step D) with $R^1X^1$ (where $X^1$ is a leaving group such as a halogen) to introduce $R^1$ and form the final compound.

To produce compounds in which $R^1$ is hydroxy or alkoxy the reduction and ring closure step may be effected by using a milder reducing agent (such as hydrazine in the presence of rhodium on carbon) to form, during the reaction, an intermediate having a —NHOH group (instead of an —NH2 group) at the 5-position of the benzene ring so that on ring closure there is formed a compound having the formula

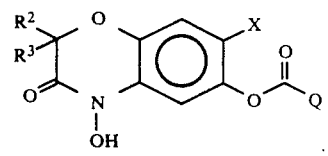

after which that compound may be treated with an appropriate alkyl halide (e.g. methyl iodide in the presence of NaH) to produce the corresponding compound in which $R^1$ is alkoxy.

To produce compounds in which $R^1$ is haloalkynyl the compound in which $R^1$ is alkynyl may be reacted with the appropriate halogen (e.g., iodine or bromine) in the presence of a base (e.g. NaOH or KOH); also a catalyst such as benzyltriethylammonium bromide or chloride or tetrabutylammonium bromide may be present.

The compound of Formula II above may be formed by reacting a phenol of the formula 2—X,4—F,-5—$NO_2C_6H_2OH$ with ClCOQ, as illustrated below in the Example. Instead of the sodium hydride used as the acid acceptor in Step A of the Example, one may use a weak base such as pyridine, preferably in an amount of at least one mole per mole of ClCOQ (the reaction may be carried out with or without additional solvent, e.g., toluene). The recovery of the product from the reaction mixture may be effected, for instance, by diluting the reaction mixture with a solvent (e.g., with ethyl acetate or methylene chloride), washing with aqueous acid and drying the organic solvent phase, followed by purification (as by chromatography, for instance).

Representative compounds of this invention are listed in Table 1 below.

The invention is illustrated further in the following Example. In this application all parts are by weight and all temperatures are in ° C. unless otherwise indicated.

EXAMPLE

(7-FLUORO-4-PROPYL-2H-1,4-BENZOXAZIN-3(4H)-ONE-6-YL) 1-PYRROLIDINECARBOXYLATE

Step A (2,4-Difluoro-5-nitrophenyl) 1-pyrrolidinecarboxylate)

To a stirred, cold (0° C.) mixture of 1.74 g of sodium hydride (0.072 mole, 2.9 g of a 60% oil suspension) and 7.0 g (0.039 mole) of 2,4-difluoro-5-nitrophenol in 100 mL of tetrahydrofuran was added 6.4 g (0.048 mole) of 1-pyrrolidinecarbonyl chloride. The reaction mixture was allowed to warm to room temperature and was stirred for four hours. The mixture was diluted with ethyl acetate and was washed with an aqueous 10% hydrochloric acid solution. The organic phase was dried over anhydrous magnesium sulfate, filtered and filtrate evaporated under reduced pressure leaving a semi-solid residue. The residue was purified by column chromatography on silica gel, eluting with ethyl acetate:n-heptane (50:50) to yield 7.2 g of (2,4-difluoro-5-nitrophenyl) 1-pyrrolidinecarboxylate. The nmr and ir spectra were consistent with the proposed structure.

Step B (2-Fluoro-4-methoxycarbonylmethoxy-5-nitrophenyl) 1-pyrrolidinecarboxylate)

To a stirred, cold (−50°) mixture of 7.00 g (0.0257 mole) of (2,4-difluoro-5-nitrophenyl) 1-pyrrolidinecarboxylate and 1.60 g (0.0283 mole) of methyl glycolate in 200 mL of tetrahydrofuran was added 1.02 g (0.0424 mole) of sodium hydride. The reaction mixture was stirred at −50° C. for approximately four hours. The mixture was allowed to gradually warm to room temperature. The reaction mixture was poured into icewater, and the resultant mixture was extracted with diethyl ether. The extract was dried over anhydrous magnesium sulfate, filtered and the filtrate evaporated under reduced pressure to yield 4.5 g of (2-fluoro-4-methoxycarbonylmethoxy-5-nitrophenyl) 1-pyrrolidinecarboxylate. The nmr and ir spectra were consistent with the proposed structure.

Step C (7-Fluoro-2H-1,4-benzoxazin-3(4H)-one-6-yl) 1-pyrrolidinecarboxylate The hydrogenation of 4.00 g (0.0117 mole) of 2-fluoro-4-methoxycarbonylmethoxy-5-nitrophenyl 1-pyrrolidinecarboxylate with 0.25 g (0.0011 mole) of platinum (IV) oxide in 150 mL of acetic acid produced 2.65 g of 7-fluoro-2H-1,4-benzoxazin-3(4H)-one-6-yl 1-pyrrolidinecarboxylate, Compound 1 of Table 1. The nmr and ir spectra were consistent with the proposed structure.

Step D (7-Fluoro-4-propyl-2H-1,4-benzoxazin-3 (4H)-one-6-yl) 1-pyrrolidinecarboxylate A stirred mixture of 0.70 g (0.0025 mole) of 7-fluoro-2H-1,4-benzoxazin-3(4H)-one-6-yl 1-pyrrolidinecarboxylate, 0.60 g (0.0036 mole) of 1-iodopropane, 1.1 g (0.0076 mole) of potassium carbonate, and 0.1 g (0.00038 mole) of 18-crown-6 in 50 mL of acetone was heated at reflux for five hours. The reaction mixture was cooled, filtered and the filtrate evaporated under reduced pressure leaving a residue. The residue was extracted with ethyl acetate. The extract was dried over anhydrous magnesium sulfate, filtered and the filtrate evaporated under reduced pressure leaving a residue. The residue was purified by column chromatography on silica gel, eluting with ethyl acetate-heptane (50:50), to yield 0.6 g of (7-fluoro-4-propyl-2H-1,4-benzoxazin-3(4H)-one-6-yl) 1-pyrrolidinecarboxylate as a solid 73°-75° C., Compound 4 of Table 1. The nmr ir spectra were consistent with the proposed structure.

HERBICIDAL ACTIVITY

The plant test species used in demonstrating the herbicidal activity of compounds of this invention include cotton (*Gossypium hirsutum var. DPLGI*), soybean (*Glycine max var. Williams*), field corn (*Zea mays var. Pioneer* 3732), wheat (*Triticum aestivium var. Wheaton*), rice (*Oryza sativa var. Labelle*), morningglory (*Ipomea lacumosa or Ipomea hederacea*), wild mustard (*Brassica kaber*), velvetleaf (*Abutilon theophrasti*), barnyardgrass (*Echinochloa crus-galli*), green foxtail (*Setaria viridis*),and johnsongrass (*Sorghum halepense*).

Preparation of Flats

Preemergence:

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilo-grams/-hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Hebicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | | % by Wt. |
|---|---|---|
| Active ingredient | | 40.00 |
| Sodium lignosulfonate | | 20.00 |
| Attapulgite clay | | 40.00 |
| | Total | 100.00 |
| Active ingredient | | 90.00 |
| Dioctyl sodium sulfosuccinate | | 0.10 |
| Synthetic fine silica | | 9.90 |
| | Total | 100.00 |
| Active ingredient | | 20.00 |
| Sodium alkylnaphthalenesulfonate | | 4.00 |
| Sodium lignosulfonate | | 4.00 |
| Low viscosity methyl cellulose | | 3.00 |
| Attapulgite clay | | 69.00 |
| | Total | 100.00 |
| Active ingredient | | 25.00 |
| Base: | | 75.00 |
| 96% hydrated aluminum magnesium silicate | | |
| 2% powdered sodium lignosulfonate | | |
| 2% powdered anionic sodium alkyl-naphthalenesulfonate | | |
| | Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | | % by Wt. |
|---|---|---|
| Active ingredient | | 53.01 |
| Blend of alkylnaphthalenesulfonate and polyoxyethylene ethers | | 6.00 |
| Epoxidized soybean oil | | 1.00 |
| Xylene | | 39.99 |
| | Total | 100.00 |
| Active ingredient | | 10.00 |
| Blend of alkylnaphthalenesulfonate and polyoxyethylene ethers | | 4.00 |
| Xylene | | 86.00 |
| | Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | | % by Wt. |
|---|---|---|
| Active ingredient | | 46.00 |
| Colloidal magnesium aluminum silicate | | 0.40 |
| Sodium alkylnaphthalenesulfonate | | 2.00 |
| Paraformaldehyde | | 0.10 |
| Water | | 40.70 |
| Propylene glycol | | 7.50 |
| Acetylenic alcohols | | 2.50 |
| Xanthan gum | | 0.80 |
| | Total | 100.00 |
| Active ingredient | | 45.00 |
| Water | | 48.50 |
| Purified smectite clay | | 2.00 |
| Xanthan gum | | 0.50 |
| Sodium alkylnaphthalenesulfonate | | 1.00 |
| Acetylenic alcohols | | 3.00 |
| | Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| Oil Suspension: | | % by Wt. |
|---|---|---|
| Active ingredient | | 25.00 |
| Polyoxyethylene sorbitol hexaoleate | | 5.00 |
| Highly aliphatic hydrocarbon oil | | 70.00 |
| | Total | 100.00 |

| Aqueous Suspension: | | % by Wt. |
|---|---|---|
| Active ingredient | | 40.00 |
| Polyacrylic acid thickener | | 0.30 |
| Dodecylphenol polyethylene glycol ether | | 0.50 |
| Disodium phosphate | | 1.00 |
| Monosodium phosphate | | 0.50 |
| Polyvinyl alcohol | | 1.00 |
| Water | | 56.70 |
| | Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 7 of the tables below has, in greenhouse testing at pre- and post-emergence dosages as low as about 0.03 to 0.13 kg/ha, given good weed control with little or no damage to soybeans wheat and corn. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

| Cmpd. No. | X | $R^1$ | Q |
|---|---|---|---|
| 1 | F | H | a |
| 2 | F | $CH_3$ | a |
| 3 | F | $CH_2CH_3$ | a |
| 4 | F | $CH_2CH_2CH_3$ | a |
| 5 | F | $CH(CH_3)_2$ | a |
| 6 | F | $CH_2CH=CH_2$ | a |
| 7 | F | $CH_2C\equiv CH$ | a |
| 8 | F | $CH_2CN$ | a |
| 9 | F | $CH_2COCH_3$ | a |
| 10 | F | $CH_2SCH_3$ | a |
| 11 | F | $CH_2C\equiv CH$ | b |
| 12 | F | $CH_2CH=CH_2$ | b |
| 13 | F | $CH_2CH_2CH_3$ | b |
| 14 | F | $CH_2CO_2H$ | a |
| 15 | F | $CH_2CO_2CH_3$ | a |
| 16 | F | $CH(CH_3)CN$ | a |
| 17 | F | $CH(CH_3)CO_2H$ | a |
| 18 | F | $CH_2CH_2CH_2Cl$ | a |
| 19 | F | $CH_2C(Cl)=CH_2$ | a |
| 20 | F | $CH_2C\equiv CBr$ | a |
| 21 | F | $CH_2OCH_3$ | a |
| 22 | F | $CH_2OCH_2OCH_2CH_3$ | a |
| 23 | F | $CH_2$-cyclopropyl | a |
| 24 | F | $CH_2C_6H_5$ | a |
| 25 | Cl | $CH_2SCH_3$ | a |
| 26 | Cl | $CH_2C\equiv CH$ | a |
| 27 | Br | $CH_2C\equiv CH$ | a |
| 28 | F | $CH_2C\equiv CH$ | c |

$R^2$ and $R^3$ are each H;

Q is (a) N⟨ ⟩, (b) N⟨ ⟩O, or (c) N⟨ ⟩S.

TABLE 2

Identifying Properties

| Cmpd No. | M.P.(°C.) | Empirical Formula | Elemental Analysis | | |
|---|---|---|---|---|---|
| | | | C | H | N |
| 1 | 185–186.5 | $C_{13}H_{13}FN_2O_4$ | C 55.71 | 4.68 | 10.00 |
| | | | F 55.67 | 4.46 | 9.79 |
| 2 | 141–143 | $C_{14}H_{15}FN_2O_4$ | C 57.14 | 5.14 | 9.52 |
| | | | F 56.44 | 5.36 | 9.01 |
| 3 | 138–139.5 | $C_{15}H_{17}FN_2O_4$ | C 58.44 | 5.56 | 9.09 |
| | | | F 58.71 | 5.56 | 9.03 |
| 4 | oil | $C_{16}H_{19}FN_2O_4$ | C 59.62 | 5.94 | 8.69 |
| | | | F 59.75 | 5.86 | 8.42 |
| 5 | 110–111 | $C_{16}H_{19}FN_2O_4$ | C 58.44 | 5.56 | 9.09 |
| | | | F 59.13 | 5.86 | 8.65 |
| 6 | 96–97 | $C_{16}H_{17}FN_2O_4$ | C 60.00 | 5.35 | 8.75 |
| | | | F 59.80 | 5.27 | 8.59 |
| 7 | 163–165 | $C_{16}H_{15}FN_2O_4$ | C 60.37 | 4.75 | 8.80 |
| | | | F 59.67 | 4.50 | 9.59 |
| 8 | 191.5–192 | $C_{15}H_{14}FN_3O_4$ | C 56.43 | 4.42 | 13.16 |
| | | | F 55.95 | 4.02 | 12.84 |
| 9 | 121.5–123 | $C_{16}H_{17}FN_2O_5$ | C 60.56 | 5.40 | 8.83 |
| | | | F 56.45 | 5.04 | 7.13 |
| 10 | 148 | $C_{15}H_{17}FN_2O_4S$ | C 52.93 | 5.03 | 8.23 |
| | | | F 52.99 | 4.79 | 8.46 |
| 11 | 163–164 | $C_{16}H_{15}FN_2O_5$ | C 57.49 | 4.52 | 8.38 |
| | | | F 57.63 | 4.63 | 8.50 |
| 12 | 123–124 | $C_{16}H_{17}FN_2O_5$ | C 57.14 | 5.10 | 8.33 |
| | | | F 57.18 | 5.05 | 8.26 |
| 13 | 110–111 | $C_{16}H_{19}FN_2O_5$ | C 56.80 | 5.66 | 8.28 |
| | | | F 57.10 | 5.79 | 8.21 |

TABLE 3

PREEMERGENCE HERBICIDAL ACTIVITY (% CONTROL)

| | Compound No. | | | | | | |
|---|---|---|---|---|---|---|---|
| | 1 | 2 | 3 | 4 | 5 | 6 | 7 |
| | Rate (kg/ha) | | | | | | |
| | 2.0 | 0.125 | 0.125 | 0.5 | 0.125 | 1.125 | 1.0 |
| Cotton | 15 | 10 | 35 | 20 | 15 | 20 | 100 |
| Soybean | 70 | 10 | 15 | 10 | 20 | 15 | 100 |
| Corn | 85 | 15 | 70 | 70 | 50 | 85 | 85 |
| Rice | 95 | 10 | 60 | 95 | 70 | 80 | 100 |
| Wheat | 70 | 15 | 60 | 70 | 35 | 85 | 95 |
| Morningglory | 50 | 20 | 20 | 70 | 50 | 70 | 100 |
| Wild Mustard | 90 | 20 | 50 | 50 | 10 | 20 | 100 |
| Velvetleaf | 100 | 60 | 100 | 100 | 100 | 100 | 100 |
| Barnyardgrass | 95 | 10 | 85 | 95 | 50 | 100 | 100 |
| Green Foxtail | 100 | 85 | 90 | 100 | 20 | 90 | 100 |
| Johnsongrass | 95 | 30 | 20 | 80 | 50 | 60 | 100 |

| | Compound No. | | | | | |
|---|---|---|---|---|---|---|
| | 8 | 9 | 10 | 11 | 12 | 13 |
| | Rate (kg/ha) | | | | | |
| | 0.125 | 0.125 | 0.125 | 0.5 | 0.5 | 0.5 |
| Cotton | 20 | 40 | 5 | 70 | 15 | 0 |
| Soybean | 35 | 30 | 15 | 40 | 30 | 0 |
| Corn | 70 | 70 | 15 | 100 | 60 | 15 |
| Rice | 70 | 70 | 10 | 95 | 90 | 30 |
| Wheat | 50 | 50 | 15 | 100 | 90 | 15 |
| Morningglory | 70 | 85 | 20 | 40 | 20 | 20 |
| Wild Mustard | 40 | 30 | 10 | 95 | 30 | 5 |
| Velvetleaf | 100 | 100 | 95 | 100 | 100 | 90 |
| Barnyardgrass | 95 | 95 | 50 | 100 | 95 | 30 |
| Green Foxtail | 95 | 50 | 60 | 100 | 100 | 95 |
| Johnsongrass | 70 | 60 | 20 | 95 | 100 | 90 |

TABLE 4

POSTEMERGENCE HERBICIDAL ACTIVITY (% CONTROL)

| | Compound No. | | | | | | |
|---|---|---|---|---|---|---|---|
| | 1 | 2 | 3 | 4 | 5 | 6 | 7 |
| | Rate (kg/ha) | | | | | | |
| | 2.0 | 0.125 | 0.125 | 0.5 | 0.125 | 1.125 | 1.0 |
| Cotton | 100 | 30 | 95 | 100 | 95 | 95 | 100 |
| Soybean | 80 | 40 | 60 | 85 | 30 | 70 | 100 |
| Corn | 70 | 60 | 50 | 70 | 60 | 70 | 100 |
| Rice | 30 | 40 | 0 | 90 | 50 | 40 | 100 |
| Wheat | 70 | 0 | 0 | 70 | 10 | 15 | 100 |
| Morningglory | 95 | 0 | 60 | 95 | 40 | 100 | 100 |
| Wild Mustard | 20 | 0 | 0 | 30 | 30 | 40 | 100 |
| Velvetleaf | 100 | 0 | 100 | 100 | 100 | 100 | 100 |
| Barnyardgrass | 40 | 0 | 40 | 95 | 20 | 40 | 100 |
| Green Foxtail | 95 | ND* | 70 | 85 | 80 | 60 | 100 |
| Johnsongrass | 50 | 0 | 40 | 40 | 50 | 40 | 100 |

TABLE 4-continued
POSTEMERGENCE HERBICIDAL ACTIVITY (% CONTROL)

| | Compound No. | | | | | |
|---|---|---|---|---|---|---|
| | 8 | 9 | 10 | 11 | 12 | 13 |
| | Rate (kg/ha) | | | | | |
| | 0.125 | 0.125 | 0.125 | 0.5 | 0.5 | 0.5 |
| Cotton | 95 | 90 | 80 | 100 | 90 | 100 |
| Soybean | 70 | 60 | 50 | 70 | 60 | 60 |
| Corn | 80 | 90 | 70 | 70 | 85 | 40 |
| Rice | 20 | 10 | 10 | 85 | 40 | 5 |
| Wheat | 0 | 0 | 30 | 90 | 40 | 10 |
| Morningglory | 100 | 100 | 70 | 90 | 100 | 90 |
| Wild Mustard | 20 | 10 | 20 | 85 | 5 | 10 |
| Velvetleaf | 100 | 100 | 95 | 100 | 100 | 100 |
| Barnyardgrass | 20 | 50 | 30 | 70 | 10 | 5 |
| Green Foxtail | 70 | 20 | 30 | 95 | 95 | 85 |
| Johnsongrass | 40 | 40 | 30 | 90 | 70 | 10 |

I claim:

1. Compound of the formula

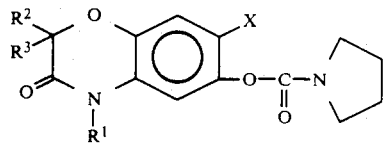

in which $R^1$ is H, alkyl, alkenyl, alkynyl, haloalkyl, haloalkenyl, haloalkynyl, alkoxyalkyl, alkoxyalkoxyalkyl, cycloalkyl, aralkyl, alkylthioalkyl, hydroxy, alkoxy, cyanoalkyl or alkylcarbonylalkyl;

$R^2$ and $R^3$ are independently H or alkyl;

X is H, Cl or F; and in which any alkyl, alkenyl, alkynyl or alkylene moiety of $R^1$, $R^2$ or $R^3$ have less than 6 carbon atoms.

2. Compound as in claim 1 in which $R^1$ is propargyl.

3. An herbicidal composition comprising an herbicidally effective amount of the compound of claim 1 in admixture with a suitable carrier.

4. A method for controlling undesired plant growth with comprises applying to the locus where control is desired an herbicidally effective amount of the composition of claim 3.

5. An herbicidal composition comprising an herbically effective amount of the compound of claim 2 in admixture with a suitable carrier.

6. A method for controlling undesired plant growth with comprises applying to the locus where control is desired an herbicidally effective amount of the composition of claim 5.

* * * * *

UNITED STATES PATENT AND TRADEMARK OFFICE
CERTIFICATE OF CORRECTION

PATENT NO. : 4,994,104
DATED : February 19, 1991
INVENTOR(S) : Jun H. Chang

It is certified that error appears in the above-identified patent and that said Letters Patent is hereby corrected as shown below:

On the title page:

On the title page, item [54], and in column 1, lines 2-3, change the title "TETRAHYDROPHTHALIMIDE CARBAMATE HERBICIDAL COMPOSITIONS"

to read -- BENZOXAZINONYL PYRROLIDINECARBOXYLATE HERBICIDAL COMPOSITIONS -- .

Column 1, line 27, after "alkyl", please insert a comma.

Signed and Sealed this

Eleventh Day of August, 1992

Attest:

DOUGLAS B. COMER

Attesting Officer

Acting Commissioner of Patents and Trademarks